United States Patent
Sossong et al.

(10) Patent No.: US 10,555,709 B2
(45) Date of Patent: Feb. 11, 2020

(54) CHARGED PARTICLE TOMOGRAPHY SCANNER FOR REAL-TIME VOLUMETRIC RADIATION DOSE MONITORING AND CONTROL

(71) Applicant: Decision Sciences International Corporation, Poway, CA (US)

(72) Inventors: Michael James Sossong, Ramona, CA (US); Weidong Luo, Poway, CA (US)

(73) Assignee: Decision Sciences International Corporation, Poway, CA (US)

( * ) Notice: Subject to any disclaimer, the term of this patent is extended or adjusted under 35 U.S.C. 154(b) by 1185 days.

(21) Appl. No.: 14/634,808

(22) Filed: Feb. 28, 2015

(65) Prior Publication Data

US 2015/0246244 A1    Sep. 3, 2015

Related U.S. Application Data

(60) Provisional application No. 61/946,692, filed on Feb. 28, 2014.

(51) Int. Cl.
*A61B 6/00* (2006.01)
*A61N 5/10* (2006.01)
(Continued)

(52) U.S. Cl.
CPC ............ *A61B 6/4266* (2013.01); *A61B 6/032* (2013.01); *A61B 6/4258* (2013.01);
(Continued)

(58) Field of Classification Search
None
See application file for complete search history.

(56) References Cited

U.S. PATENT DOCUMENTS 4,190,772 A    2/1980    Dinwiddie et al.
4,484,571 A    11/1984   Velazquez
(Continued)

FOREIGN PATENT DOCUMENTS

WO    2009/002602 A2    12/2008

OTHER PUBLICATIONS

Cuttler, J.M., et al., "Nuclear Energy and Health: And the Benefits of Low-Dose Radiation Hormesis," Dose Response, 7(1):52-89, Nov. 2008.
(Continued)

*Primary Examiner* — Katherine L Fernandez
(74) *Attorney, Agent, or Firm* — Perkins Coie LLP (57) ABSTRACT

In one aspect, a charged particle tomography and radiation therapy system includes a charged particle tomography scanner (CPTS) unit to detect at least some of the charged particles of an emitted charged particle beam delivered to a region of interest of a subject. A processing unit can determine energy loss of the charged particle beam based on the detected trajectory information. An incoming detector is positioned to detect trajectory information of the at least some of the charged particles entering the subject. An outgoing detector is positioned to detect trajectory information of the at least some of the charged particles passing through and exiting the subject. A motion control unit can control movement of the incoming and outgoing detectors. The incoming and outgoing detectors are sized to cover at least an area substantially equivalent to the beam's cross-section. The processing unit can map radiation dose of the region of interest.

20 Claims, 3 Drawing Sheets

(51) Int. Cl.
*A61B 6/03* (2006.01)
*A61B 6/12* (2006.01)

(52) U.S. Cl.
CPC .......... *A61B 6/5205* (2013.01); *A61B 6/5235* (2013.01); *A61B 6/542* (2013.01); *A61N 5/1067* (2013.01); *A61N 5/1071* (2013.01); *A61B 6/12* (2013.01); *A61B 6/469* (2013.01); *A61N 2005/1054* (2013.01); *A61N 2005/1087* (2013.01)

(56) References Cited

U.S. PATENT DOCUMENTS

| | | | |
|---|---|---|---|
| 4,649,504 A | 3/1987 | Krouglicof et al. | |
| 5,811,944 A | 9/1998 | Sampayan et al. | |
| 6,316,776 B1* | 11/2001 | Hiramoto | A61N 5/1042 250/492.3 |
| 6,879,160 B2 | 4/2005 | Jakab | |
| 7,336,763 B2 | 2/2008 | Spartiotis et al. | |
| 8,121,361 B2 | 2/2012 | Ernst et al. | |
| 8,536,527 B2* | 9/2013 | Morris | G01N 23/046 250/306 |
| 8,552,370 B2 | 10/2013 | Schultz et al. | |
| 2003/0205675 A1* | 11/2003 | Nelson | A61B 6/4233 250/370.09 |
| 2005/0261570 A1 | 11/2005 | Mate et al. | |
| 2006/0027766 A1* | 2/2006 | Matsuda | A61N 5/10 250/496.1 |
| 2008/0253511 A1 | 10/2008 | Boyden | |
| 2010/0016865 A1 | 1/2010 | Kieper | |
| 2010/0195792 A1 | 8/2010 | Kunz et al. | |
| 2011/0220794 A1 | 9/2011 | Censor et al. | |
| 2013/0238291 A1* | 9/2013 | Schultz | G01N 23/20 703/2 |
| 2015/0245802 A1 | 9/2015 | Sossong et al. | |

OTHER PUBLICATIONS

Hendee, W.R., et al., "Magnetic Resonance Imaging Part I—Physical Principles," The Western Journal of Medicine, 141(4):491-500, Oct. 1984.

International Search Report and Written Opinion dated Jun. 1, 2015 for International Application No. PCT/US2015/018213, filed on Feb. 28, 2015 (9 pages).

International Search Report and Written Opinion dated Jun. 3, 2015 for International Application No. PCT/US2015/018214, filed on Feb. 28, 2015 (10 pages).

Plautz, T., et al., "200 MeV Proton Radiography Studies With a Hand Phantom Using a Prototype Proton CT Scanner," IEEE Transactions on Medical Imaging, 33(4):875-881, Apr. 2014.

Schippers, J.M., et al., "Emerging technologies in proton therapy," Acta Oncologica, 50(6):838-850, Mar. 2011.

Zhu, X., et al., Monitoring proton radiation therapy with in-room PET imaging, Physics in Medicine & Biology, 56(13):4041-4057, Jun. 2011.

* cited by examiner

CHARGED PARTICLE TOMOGRAPHY SCANNER FOR REAL-TIME VOLUMETRIC RADIATION DOSE MONITORING AND CONTROL

CROSS REFERENCE TO RELATED CASES

This patent document claims the benefit of priority of U.S. Provisional Application No. 61/946,692, filed on Feb. 28, 2014. The entire content of the before-mentioned patent application is incorporated by reference as part of the disclosure of this document.

TECHNICAL FIELD

This patent document relates to systems, devices, and processes that use relates to radiation therapy technologies.

BACKGROUND

Radiation therapy, also referred to as radiation oncology and radiotherapy, is the use of ionizing radiation, in general, to control cell growth or kill cells, e.g., such as malignant cancer cells. Ionizing radiation can function by damaging the DNA of exposed tissue, e.g., leading to cellular death. Radiation therapy typically include techniques to spare normal and/or healthy tissues (e.g., such as skin and organs that the ionized radiation passes through during the therapy. For example, such techniques can include shaped radiation beams that are aimed from several angles of exposure to intersect at the target cells, e.g., providing a much larger absorbed dose at the target cells than in the surrounding, healthy tissue. In some treatments, radiation therapy can be combined with other therapies including surgery, chemotherapy, hormone therapy, immunotherapy, or some mixture of the four. Some examples of existing radiation therapies include total body irradiation (TBI), which is a radiation therapy technique used to prepare the body to receive a bone marrow transplant, and brachytherapy, in which a radiation source is placed inside or next to the area requiring treatment, e.g., to minimize exposure to healthy tissue during procedures to treat cancers of the breast, prostate and other organs.

SUMMARY

Techniques, systems, and devices are disclosed for implementing charged particle tomography for real-time volumetric radiation dose monitoring and dosage control.

In one aspect, a system includes a charged particle tomography scanner (CPTS) unit to detect individual charged particles of an emitted charged particle beam delivered to a subject by a charged particle delivery system, and a processing unit in data communication with the CPTS unit to determine energy loss of the charged particle beam based on detected trajectory information. The CPTS unit including a first detector positioned between the subject and the charged particle delivery system to receive and detect trajectory information of the individual charged particles of the emitted charged particle beam, a second detector positioned at a side of the subject opposite to that of the first detector to receive and detect the trajectory information of the individual charged particles of the charged particle beam having passed through the first detector and the subject, and a motion control unit configured to move the first detector and the second detector, in which the first and second detectors are of a size to cover an area at least that of the beam's cross-section. The processing unit further can map the radiation dose (e.g., produce an energy loss map) as well as generate an anatomical image.

The subject matter described in this patent document can be implemented in specific ways that provide one or more of the following features. For example, the disclosed technology includes novel methodologies and systems for accurate volumetric measurement of charged particle dose delivery. In some aspects, the disclosed technology includes a dual head charged particle tomography scanner devices and systems for real-time volumetric radiation dose measurement and dosage control. For example, an exemplary charged particle radiation therapy system includes a charged particle source and a dual head charged particle tomography scanner that measures the real time volumetric radiation dose measurement by directly measuring the charged particle beam energy loss as well as the individual track orientation changes. This information is used to provide charged particle dosage control for effective radiation treatment. For example, the disclosed charged particle tomography systems and methods can be used to visualize the particle energy deposition (dose) within the 3D volume. Implementations of the disclosed systems and methods can also provide confirmation of patient positioning based on surface attached markers or surgically implanted markers. Such systems and methods allow for a new type of personalized charged particle therapy treatment by providing verification for individual fields in a multiple field irradiation and real time adaptive monitoring of therapy. In some implementations, for example, to achieve adaptive monitoring, a small dose can be delivered and then the patient's complete dose can be delivered after the charge particle beam range has been verified.

DETAILED DESCRIPTION

Charged particle radiation therapies such as proton therapy or electron therapy have finite range in the tissue and more non-linear energy deposition along individual tracks in comparison to the X-ray or gamma ray beam treatments. This helps to reduce the damage to the critical radiation sensitive organs or tissues surrounding the target tissue, e.g., such as a tumor. However, it is difficult to estimate the dose delivery within the human body precisely due to the uncertainty resulting from multiple sources, e.g., such as beam delivery errors, patient positioning errors, treatment planning errors, motion of an organ (e.g., such as lung), or tumor shape change due to fractionated dose delivery. Among these errors, the charged particle dose delivery errors are particularly concerning if large gradients of the dose delivered near a certain finite range near Bragg peak.

Techniques, systems, and devices are disclosed for implementing charged particle tomography for real-time volumetric radiation dose monitoring and dosage control.

In some aspects, the disclosed technology includes a dual head charged particle tomography scanner devices and systems for real-time volumetric radiation dose measurement and dosage control. For example, an exemplary charged particle radiation therapy system includes a charged particle source and a dual head charged particle tomography scanner that measures the real time volumetric radiation dose measurement by directly measuring the charged particle beam energy loss as well as the individual track orientation changes. This information is used to provide charged particle dosage control for effective radiation treatment.

Currently, there are two other approaches under development for volumetric dose delivery measurement: in room PET in situ method, and Proton computed tomography (proton CT) method. For example, in room PET in situ method can only be applied to the heavy charged particle therapies, such as proton therapy. During the proton therapy, small amounts of positron emitters are produced along the beam path via different channels of nuclear fragmentation reactions. There is a unique relationship between the activity and dose distal fall-off positions which make range verification possible. Currently, the verification is carried out by comparing PET images with predicated activity distributions calculated by Monte Carlo simulations. The range is verified by comparing the distal fall-off depths of activity distribution profiles between PET measurements and Monte Carlo predictions. Also for example, proton CT method includes obtaining measured data for a plurality of protons or other heavy charged particles that pass through an object and estimating a path taken by each proton within the object based on the incident and outbound tracks. Image reconstruction algorithms are used which are similar to the conventional computed tomography. Some of the algorithms consider the relative energy deposition along the through tracks. These existing techniques, like PET in situ and proton CT methods, include several limitations and disadvantages for wide scale use.

The disclosed technology includes novel methodologies and systems for accurate volumetric measurement of charged particle dose delivery. For example, the disclosed charged particle tomography systems and methods can be used to visualize the particle energy deposition (dose) within the 3D volume. Implementations of the disclosed systems and methods can also provide confirmation of patient positioning based on surface attached markers or surgically implanted markers. Such systems and methods allow for a new type of personalized charged particle therapy treatment by providing verification for individual fields in a multiple field irradiation and real time adaptive monitoring of therapy. In some implementations, for example, to achieve adaptive monitoring, a small dose can be delivered and then the patient's complete dose can be delivered after the charge particle beam range has been verified.

Unlike existing techniques including in room/in situ PET and Proton CT methods, for example, the disclosed system and methods can be used to measure all types of charged particles including heavy charged particle (e.g., protons and carbon ions) as well as less heavy particles (e.g., such as muons and electrons). The disclosed system and methods can provide real time feedback of the radiation dose delivery. The disclosed system and methods can use reconstruction algorithms and exemplary pre-therapy planning images for additional guidance in its dose distribution reconstruction processes.

The disclosed system and methods can directly measure the beam energy loss as well as the individual track orientation changes, e.g., rather than measure the excited positrons as in PET in situ methods. Additionally, for example, the disclosed charged particle tomography technology does not suffer from substantial background radiation during beam extraction or sensitivity to the time course of irradiation that ultimately requires synchronization of data acquisition with the beam control system, as in PET in situ methods. Further disadvantages of PET in situ methods not present in the disclosed technology include the limited solid angle of data collection in PET systems resulting in reduced sensitivity and severe artifacts in reconstructed PET images; large costs of a PET unit. Additional errors might occur such as patient repositioning and anatomical changes during the patient transportation and repositioning. More importantly, the biological washout of activity can significantly affect the spatial distribution of the signal and this PET procedure significantly affects the patient throughput of proton therapy procedure.

The disclosed system and methods can be used to create three dimensional dose delivery volumetric images (stop image) based on absolute energy deposition, rather than based on relative energy deposition such as in Proton CT techniques. For example, this can allow for the real time monitoring the charged particle therapy dose delivery. Also, the disclosed system and methods can include using a planning tomography image for guiding the stop image reconstruction. For example, this can be done by (a) using the surface metal markers or surgical implant markers; (b) using a higher energy beam before the radiation therapy or allowing the outgoing detector to detect the through beam density to image those marks and/or anatomic structure; and/or (c) performing a landmark based or image volume based registration method to correlate the planning tomography image and the patient image. Moreover, the disclosed system and methods can include obtaining through track data simultaneously in some situations during the therapy. For example, an exemplary hybrid reconstruction algorithm using both the information from the through track data (scattered data) and the stopped tracks can be developed, which is different from CT image reconstruction algorithms. Furthermore, interventions based on the disclosed system and methods can be applied to electron therapy and muon therapy, e.g., which are not covered by proton CT techniques. For example, an intervention could be used in the radiation therapy site for charged particle radiation therapy quality assurance and dose delivery optimization. It can also be used as a standalone muon tomography unit for anatomical imaging or security imaging, e.g., such as scanning baggage.

In one aspect, a system includes a charged particle tomography scanner (CPTS) unit to detect individual charged particles of an emitted charged particle beam delivered to a subject by a charged particle delivery system, and a processing unit in data communication with the CPTS unit to determine energy loss of the charged particle beam based on detected trajectory information, and in some configurations, map the radiation dose (e.g., produce an energy loss map) and/or generate an anatomical image. The CPTS unit includes an incoming tracking detector positioned between the subject and the charged particle delivery system to receive and detect incident trajectory information of individual charge particles of the charged particle beam (e.g., the momentum, incident point location, and incident angle of each charged particle of the emitted charged particle beam). The CPTS unit includes an outgoing tracking detector positioned at a side of the subject opposite to that of the incoming tracking detector to receive and detect the outgoing trajectory information of the individual charged particles of the charged particle beam having passed through the incoming detector and the subject. The CPTS unit includes a motion control unit configured to move the incoming detector and outgoing detector, in which the incoming and outgoing detectors are of a size to cover an area at least that of the beam's cross-section. For example, the trajectory information can include, but is not limited to, the momentum, incident point location, and incident angle of a charged particle of the charged particle beam.

Implementations of the system can include one or more of the following exemplary features. In some implementations, for example, the processing unit can provide a control signal to the charged particle delivery system to affect the strength or direction of the emitted charged particle beam. For example, the processing unit can increase or decrease the power of the charged particle beam and/or change the aim or beam width of the charged particle beam. In some implementations, for example, the processing unit can provide a control signal to the CPTS unit to move one or both of the incoming detector and the outgoing detector in individual directions. In some implementations, for example, the system can further include a plurality of surface landmarks positioned on the subject to scatter the charged particles of the charged particle beam. For example, the processing unit can be implemented to form an image of energy disposition in a particular volume of the subject based on the detected trajectory information and scatter information of the charged particles. For example, the image can provide a guidance map to direct the charged particle beam. In some implementations, for example, the incoming detector and the outgoing detector of the CPTS unit can include ionization based position sensitive detector arrays. For example, the ionization based position sensitive detector arrays can include scintillation fiber, drift cells and/or resistive plate chambers, time projection chambers (TPCs) and/or tracing detectors. In some implementations, for example, the system can further include one or more securement units to attach the subject to a surface in a substantially motionless position.

Charged Particle Tomography and Therapy System

Figure 1A:
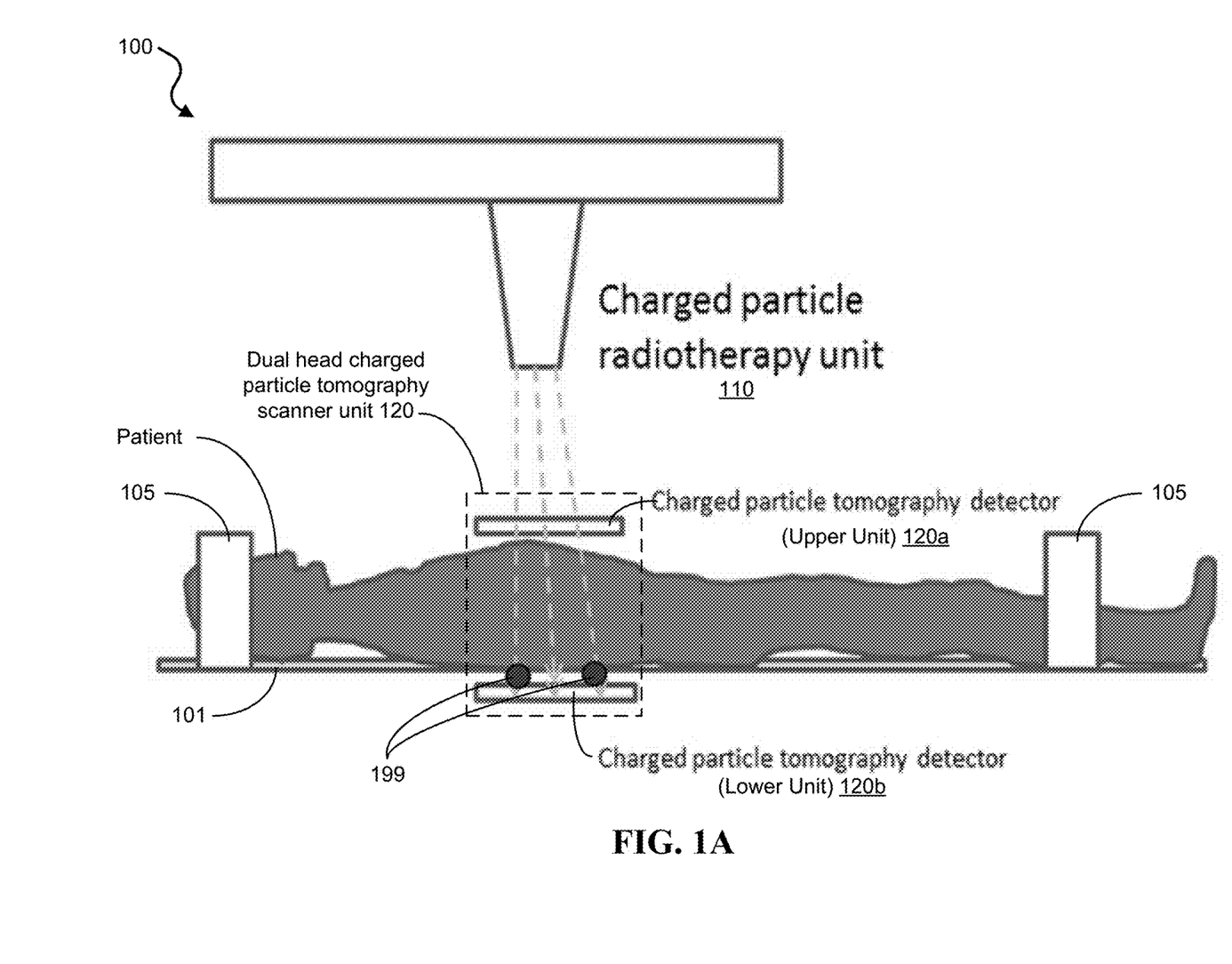
FIG. 1A shows a diagram of an exemplary charged particle tomography system for volumetric dose monitoring and control.

FIG. 1A shows a diagram of an exemplary charged particle tomography and therapy system 100 for volumetric dose monitoring and control. As shown in the diagram, a patient is positioned horizontally on a table or surface 101, for example, for a charged particle based tomography and therapy intervention. In other examples, the patient can be positioned in other postures and orientations, e.g., including vertical. The exemplary system 100 includes a dual head charged particle tomography scanner unit 120 having a field of view covering at least the radiation beam cross-section and a mechanism to be able to move the scanner relative to the beam movement. The charged particle tomography scanner unit 120 can detect the individual charged particles of an emitted charged particle radiation beam delivered by a charged particle therapy unit 110 at the patient (e.g., positioned on the surface 101). In general, the charged particle radiotherapy unit 110 can include an accelerator, beam guide, and other units to direct the charge particle beam having a determined magnitude or power. For example, the charged particle radiotherapy unit 110 can include particle therapy and proton therapy machines and systems, e.g., such as those described in U.S. Pat. No. 5,811,944 and a review article entitled "Emerging technologies in proton therapy" by Jacobus M. Schippers and Antony J. Lomax published in Acta Oncologica, volume 50, No. 6, pages 838-850 in 2011, which are included as part of the disclosure of this patent document.

The charged particle radiotherapy unit 110 can be implemented using a various types of particle therapy and proton therapy machines that include a particle accelerator. Examples of the particle accelerator can include a synchrotron or cyclotron accelerator that accelerates a beam of charged particles, such as protons, to a desired energy level for use in radiotherapy, including active pencil beam scanning and passive scattering. The synchrotron accelerator can be implemented as a ring structure that receives particles from a pre-accelerator, stores the received particles, and accelerates the stored particles to a desired energy. When the desired energy is reached, the accelerated particles are applied to a patient for radiotherapy treatment. Any unused particles in the ring are decelerated and removed. The cyclotron accelerator can be implemented as a large magnet, such as a superconducting magnet, that accelerates the particles to a fixed energy level associated the particular cyclotron accelerator. The accelerated particles from the cyclotron accelerator are slowed down by a degrader to a desired energy level. The degrader can include a variable amount of material, such as graphite. The degrader can be coupled to a collimation system and a magnetic analyzer to select the desired energy level and energy spread of the beam of charged particles applied to a patient for radiotherapy treatment.

Another example of the particle accelerator include a Fixed Field Alternating Gradient (FFAG) accelerator, which is a synchrocyclotron with a stronger focusing achieved by splitting up the magnet into separate sector magnets of alternating magnetic field. The cavity and RF-generator in the FFAG accelerator are more complicated than the synchrocyclotron due to the much stronger electric field requirement. The FFAG accelerator can achieve higher beam intensities than synchrocyclotrons, and allows for particle extraction at arbitrary energies by switching off the RF-generator when the desired energy has been obtained.

Dielectric Wall Accelerator is yet another example of the particle accelerator that includes stacked rings of high gradient insulator (HGI) material with conducting sheets inserted at frequent intervals along the stack. Each conducting sheet is connected to a laser driven high voltage switching circuit that produces an electric field on the inner side of the HGI ring when the switches are closed. Successive closing of the switches shifts the region of strong electric field along the stack and accelerates protons traveling in phase with the shifting electric field.

In some implementations, the particle accelerators can be implemented using laser and light transmission components rather than beam line magnets. Various methods can be applied to accelerate protons using strong laser pulses. For example, using Target Normal Sheet Acceleration (TNSA) method, a high intensity laser can irradiate a front surface of a solid target saturated with hydrogen to create plasma. Electrons in the plasma emerges from a rear surface of the target inducing strong electric fields to accelerate the protons out of the rear surface of the target. Proton energies of at least 20 MeV can be achieved using a laser power intensity of $6 \times 10^{19}$ W/cm$^2$ and a pulse length of 320 fs. A laser power of $10^{22}$ W/cm$^2$ can potentially deliver a 200 MeV beam of proton. To select protons with the desired energy, dipole magnets and apertures can be used or a suitable scattering material at the location in the analyzing system to separate the charged particles in space depending on their energy.

In some implementations, radiation pressure acceleration (RPA) uses the light pressure of a laser pulse incident on a foil to accelerate the whole foil as a plasma slab. RPA can provide higher proton energies and less energy spread than TNSA.

The dual head charged particle tomography scanner unit 120 can include a charged particle tomography detector 120a positioned about the patient to receive the emitted charged particle beam and a charged particle tomography detector 120b positioned about the patient to receive the charged particle beam having passed through the incoming detector 120a and the patient. For example, in some implementations, the charged particle tomography detector 120a can be positioned above the patient who might be positioned horizontally on the surface 101 underneath the charged particle therapy unit 110, and the charged particle tomography detector 120b can be positioned below the patient, e.g., underneath the surface 101.

Figure 1B:
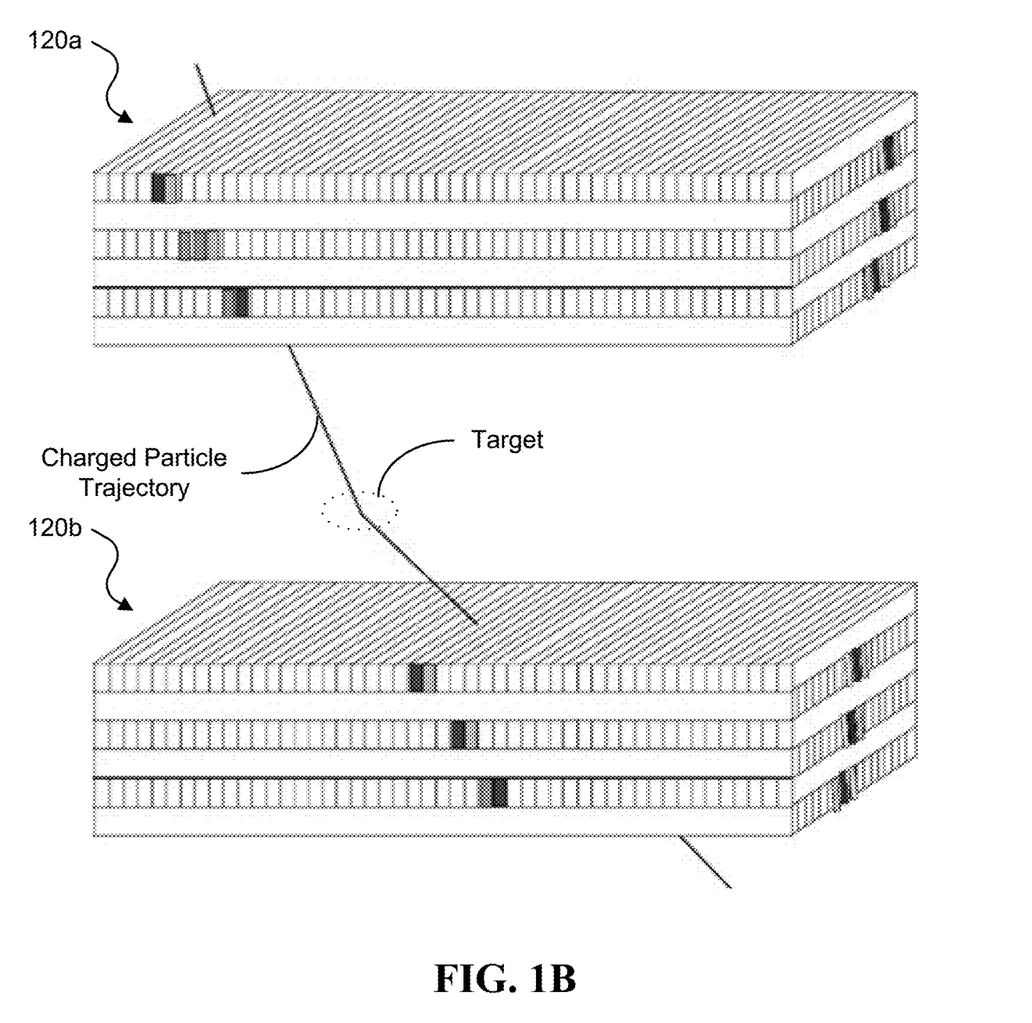
FIG. 1B shows a diagram of an exemplary charged particle tracking array including strip-type position sensitive arrays for charged particle tracking.

In some embodiments, for example, the charged particle tomography scanner unit 120 includes charged particle tracking arrays. The charged particle arrays can include multiple layers of position sensitive detector channels. For example, the charged particle tracking arrays can include one-dimensional strip-type scintillation fiber, silicon-microstrip, and/or drift cell sensors. These exemplary sensors can record the position of the charged particle as it passes through the array. Position measurements at each layer can be combined to reconstruct the trajectory of the particle in three dimensions as it was passing through the array. The sensor arrays can detect the momentum, incident point coordinates and incident angles for the incident and exit charged particles. FIG. 1B shows a diagram of an exemplary charged particle tracking array including strip-type position sensitive arrays for charged particle tracking.

In some implementations, for example, the system 100 can include securement and/or positioning units 105 to secure and/or position the patient on the table 101. The exemplary red dots 199 are surface landmarks used for image registration.

Figure 2A:
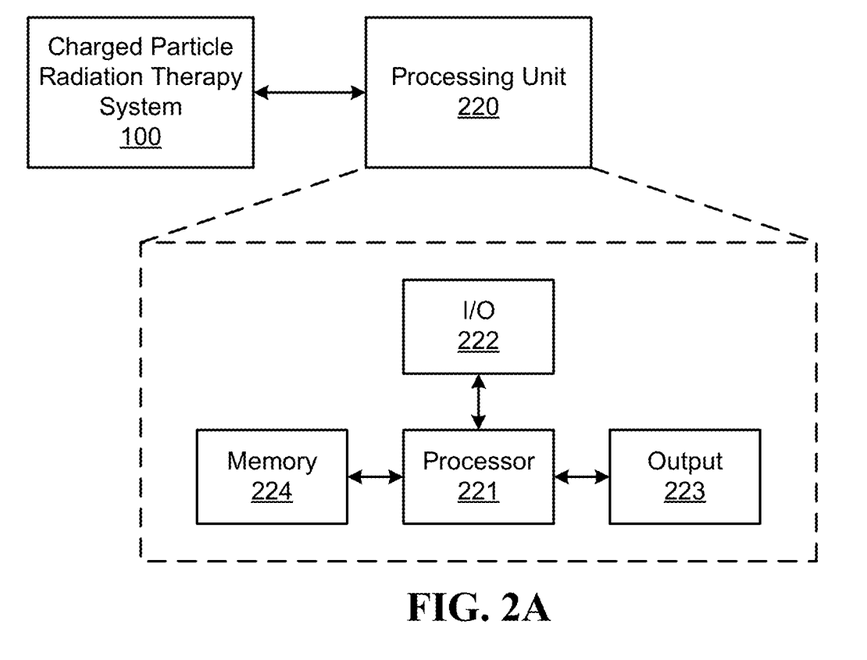
FIGS. 2A and 2B show a block diagram of an exemplary system for performing a charged particle tomography and radiation therapy treatment plan.

FIG. 2A shows a block diagram of an exemplary system 200 for performing a charged particle tomography and radiation therapy treatment plan. FIG. 2A shows an exemplary embodiment of the system 200 that may include the exemplary charged particle tomography and radiation system 100 in data communication with a processing unit 220. For example, the processing unit 220 can be in data communication with the charged particle tomography scanner unit 120 and the charged particle therapy unit 110. In some implementations, the processing unit 220 can determine the trajectory information of the individual charged particles through the detectors 120a and 120b using charged particle detection processing techniques as those described in U.S. Pat. Nos. 8,552,370 and 8,536,527, which are included as part of the disclosure of this patent document. The processing unit 220 can determine energy loss of the charged particle beam based on the detected trajectory information. Also, the processing unit can map the radiation dose (e.g., produce an energy loss map) as well as generate an anatomical image.

Charged Particle Detection Techniques

Examples of the charged particle detection processing techniques include a method for sensing a volume (e.g., body of the patient) exposed to charged particles by measuring energy loss of charged particles that enter and penetrate the volume or are stopped inside the volume without penetrating through the volume. Based on the measured energy loss, a spatial distribution of the charged particles that enter and penetrate the volume or are stopped inside the volume without penetrating through the volume can be determined. Using the spatial distribution of the energy loss of the charged particles, three-dimensional distribution of materials in the inspection volume can be reconstructed.

An exemplary tomography inspection system can include a first set of position sensitive detectors located on a first side of (e.g., above) a volume of interest (e.g., the body of a patient) to measure positions and directions of incident charged particles entering the volume of interest. A second set of position sensitive detectors can be located on a second side of (e.g., below) the volume of interest opposite to the first side to measure positions and directions of outgoing charged particles exiting the volume of interest, or the absence of charged particles that have stopped in the volume of interest. A signal processing unit can receive data of measured signals of the incoming charged particles from the first set of position sensitive detectors and measured signals of the outgoing charged particles from the second set of position sensitive detectors. The signal processing unit can analyze behaviors of the charged particles caused by interactions with physiological structures, tissues and organs within the volume of interest based on the measured incoming and outgoing positions and directions of charged particles to obtain a tomographic profile or the spatial distribution of the physiological structures, tissues and organs within the volume of interest. The signal processing unit can measure energy loss of charged particles that enter the volume and penetrate through the volume of interest, and charged particles that are stopped inside the volume of interest without penetrating through the volume. The signal processing unit can determine a spatial distribution of the charged particles that enter the volume of interest and penetrate through the volume and charged particles that are stopped inside the volume of interest without penetrating through the volume. The signal processing unit can, based on the measured energy loss, use the spatial distribution to reconstruct the spatial distribution of materials within the inspection volume.

In another aspect, a method for sensing a volume exposed to charged particles include using a first set of position sensitive detectors located on a first side of (e.g., above) the volume of interest (e.g., body of a patient) to measure positions and directions of incident charged particles that penetrate the first set of position sensitive detectors to enter the volume. The particle detection method can include using a second set of position sensitive detectors located on a second side of (e.g., below) the volume of interest opposite to the first side to measure positions and directions of outgoing charged particles exiting the volume of interest or the lack thereof. The particle detection method can include using measurements made by the second set of position sensitive detectors to determine incident charged particles that enter the volume of interest and penetrate through the volume of interest in addition to charged particles that do not penetrate through the volume of interest to reach the second set of position sensitive detectors. The particle detection method can include determining energy loss of charged particles that enter the volume of interest and penetrate through the volume of interest in addition to charged particles that are stopped inside the volume of interest without penetrating through the volume of interest. The particle detection method can include determining, based on the measured energy loss, a spatial distribution of the charged particles that enter the volume of interest and are stopped inside the volume of interest without penetrating through the volume of interest. The particle detection method can include using the spatial distribution of charged particles that enter the volume of interest and are stopped inside the volume of interest to reconstruct the spatial distribution of materials in the inspection volume.

In another aspect, a method for sensing a volume of interest (e.g., body of a patient) exposed to charged particles can include measuring energy loss of charged particles that enter the volume of interest and are stopped inside the volume of interest without penetrating through the volume of interest. The method of sensing the volume of interest can include, based on the measured energy loss, determining a spatial distribution of the charged particles that enter the volume and are stopped inside the volume without penetrating through the volume. The method of sensing the volume of interest can include using the spatial distribution to reconstruct the three dimensional spatial distribution of materials in the volume according to their respective densities and atomic numbers. From this spatial distribution, objects can be detected according to their atomic number and density.

In another aspect, a method for sensing a volume of interest exposed to charged particles can include measuring energy loss of charged particles that enter the volume of interest and are stopped inside the volume of interest without penetrating through the volume of interest. The method of sensing the volume of interest can include, based on the measured energy loss, determining a spatial distribution of the charged particles that enter the volume of interest and are stopped inside the volume of interest without penetrating through the volume of interest. The method of sensing the volume of interest can include using the spatial distribution to detect presence of one or more low density materials with low atomic numbers.

In another aspect, a method for sensing a volume of interest (e.g., body of a patient) exposed to charged particles can include using a first set of position sensitive detectors located on a first side of (e.g., above) the volume of interest to measure positions and directions of incident charged particles that penetrate the first set of position sensitive detectors to enter the volume of interest. The method for sensing a volume of interest can include using a second set of position sensitive detectors located on a second side of (e.g., below) the volume opposite to the first side to measure positions and directions of outgoing charged particles exiting the volume of interest. Using measurements made by the second set of position sensitive detectors, incident charted particles that enter the volume of interest and do not penetrate through the volume of interest to reach the second set of position sensitive detectors can be detected. The method of sensing the volume of interest can include determining energy loss of charged particles that enter the volume of interest and are stopped inside the volume of interest without penetrating through the volume of interest. The method of sensing the volume of interest can include determining, based on the measured energy loss, a spatial distribution of the charged particles that enter the volume of interest and are stopped inside the volume of interest without penetrating through the volume of interest. The method of sensing the volume of interest can include using the spatial distribution to reconstruct the three dimensional spatial distribution of materials in the volume of interest according to their density and atomic number. From this spatial distribution, objects can be detected according to their atomic number and density.

In another aspect, a method for obtaining tomographic images of a volume under inspection is provided to include detecting an incoming momentum of each incoming charged particles. The method for obtaining tomographic images of a volume under inspection includes detecting an outgoing momentum of each outgoing charged particle. The method of for obtaining tomographic images of a volume under inspection includes calculating an energy loss based on the detected incoming and outgoing momenta. The method for obtaining tomographic images of a volume under inspection includes using the calculated energy loss to reconstruct the three dimensional spatial distribution of materials in the volume according to their density and atomic number. From this spatial distribution, objects can be detected according to their atomic number and density.

In yet another aspect, the information measured in both penetrated charged particles and trapped charged particles of a volume of interest can be used to construct tomographic images of the volume. Based on the measurements of the penetrated and stopped charged particles, a processing unit can combine two or three types of measured data of trajectory changes of penetrated charged particles (e.g., penetrated muons), the information on stopped charged particles that are trapped inside the volume of interest (e.g., trapped muons), and the information on energy loss of penetrated charged particles (e.g., penetrated muons) to construct a tomographic image of the volume of interest. This process uses information of different processes inside the volume of interest to improve the fidelity and resolution of the final image for the volume of interest and to reduce the false detection.

The system 100 can be used to apply any of the methods for charged particle detection described in this patent document for curative or adjuvant treatment plans through the emission of charged particle radiation directed at target tissue or cells (e.g., including abnormal cells, such as diseased cells or cancer cells). The system 100 can be used in system 200 to implement a charged particle radiation therapy treatment process under the control of the processing unit 220. For example, the processing unit 220 can include a detector readout, digital signal processing and center data processing unit, the GUI and post processing consoles. The charged particle tomography detector unit 120 can be configured as have a mechanical structure such as a C-arm to provide the incoming and outgoing tracking units 120a and 120b of the detector 120, and a motor control system in communication with the processing unit 220 to allow the detector following the motion of the beam.

The processing unit 220 can include a processor 221 that can be in communication with an input/output (I/O) unit 222, an output unit 223, and a memory unit 224. The processing unit 220 can be implemented as one of various data processing systems, such as a personal computer (PC), laptop, and mobile communication device. To support various functions of the processing unit 220, the processor 221 can be included to interface with and control operations of other components of the processing unit 220, such as the I/O unit 222, the output unit 223, and the memory unit 224.

To support various functions of the processing unit 220, the memory unit 224 can store other information and data, such as instructions, software, values, images, and other data processed or referenced by the processor 221. Various types of Random Access Memory (RAM) devices, Read Only Memory (ROM) devices, Flash Memory devices, and other suitable storage media can be used to implement storage functions of the memory unit 224. The memory unit 224 can store radiation therapy data and information, which can include patient diagnostic data, patient image data, dosimetry data, prescription data, charged particle radiation therapy machine system parameters, and hardware constraints, which can be used in the implementation of the disclosed charged particle radiation therapy treatment plan.

The memory unit 224 can store data and information that can be used to implement the disclosed charged particle radiation therapy treatment plan and that can be generated from the charged particle radiation therapy treatment plan.

To support various functions of the processing unit 220, the I/O unit 222 can be connected to an external interface, source of data storage, or display device. Various types of wired or wireless interfaces compatible with typical data communication standards, such as Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces, can be used to implement the I/O unit 222. The I/O unit 222 can interface with an external interface, source of data storage, or display device to retrieve and transfer data and information that can be processed by the processor 221, stored in the memory unit 224, or exhibited on the output unit 223.

To support various functions of the processing unit 220, the output unit 223 can be used to exhibit data implemented by the processing unit 220. The output unit 223 can include various types of display, speaker, or printing interfaces to implement the output unit 223. For example, the output unit 223 can include cathode ray tube (CRT), light emitting diode (LED), or liquid crystal display (LCD) monitor or screen as a visual display to implement the output unit 223. In other examples, the output unit 223 can include toner, liquid inkjet, solid ink, dye sublimation, inkless (e.g., such as thermal or UV) printing apparatuses to implement the output unit 223; the output unit 223 can include various types of audio signal transducer apparatuses to implement the output unit 223. The output unit 223 can exhibit data and information, such as patient diagnostic data, charged particle radiation therapy system information, a partially processed charged particle radiation therapy treatment plan, and a completely processed charged particle radiation therapy treatment plan. The output unit 223 can store data and information used to implement the disclosed charged particle radiation therapy treatment plan and from an implemented charged particle radiation therapy treatment plan.

Figure 2B:
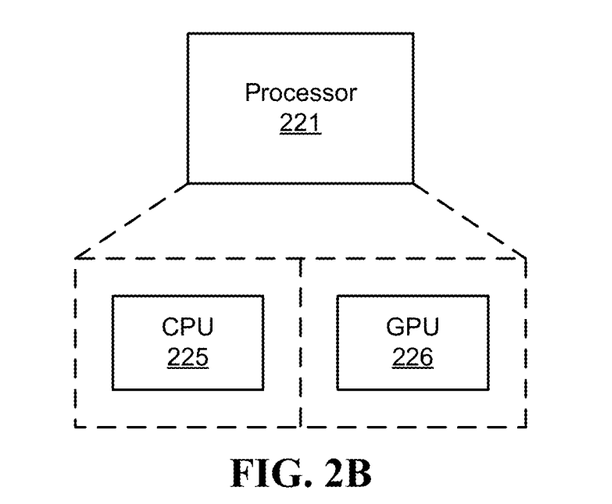

FIG. 2B shows a block diagram of the processor 221 that can include a CPU 225 or a graphic processing unit (GPU) 226, or both the CPU 225 and the GPU 226. The CPU 225 and GPU 226 can interface with and control operations of other components of the processing unit 220, such as the I/O unit 222, the output unit 223, and the memory unit 224.

Implementations of the system 200 to perform a charged particle radiation therapy treatment plan can include the following techniques. For example, a patient can be labeled with multiple surface markers 199 that can be distinguished in charged particle tomography implemented by the system 200. For example, the patient can be imaged with those surface landmarks labeled during the pre-therapy planning in order to perform the image registration.

For example, in some implementations, the charged particle tomography can be performed using muons. A muon is a charged particle with a unitary negative charge and a spin similar to an electron, but with a mass more than two hundred times greater than an electron. Muons can be generated by cosmic rays hitting the atmosphere and such cosmic-ray generated muons penetrate to the Earth's surface. As a muon moves through material, Coulomb scattering off of the charges of sub-atomic particles perturb its trajectory. The total deflection depends on several material properties, but the dominant effects are the atomic number, Z, of nuclei and the density of the material. Each muon carries information about the objects that it has penetrated. The scattering of multiple muons can be measured and processed to probe the properties of these objects. For example, a material with a high atomic number Z and/or a high density can be detected and identified when the material is located, inside low-Z and medium-Z matter. Additional information on muon tomography detection systems is described in PCT Patent Publication WO 2009/002602, entitled "IMAGING AND SENSING BASED ON MUON TOMOGRAPHY".

Muon Tomography Detection System

In an exemplary muon tomography detection system, a set of two or more planes of position-sensitive muon detectors can be arranged above a volume or region of interest to be imaged for providing the position and angles (i.e., directions in the 3-D space) of incoming muon tracks. The muon detectors can measure the position and angles of incoming muon tracks with respect to two different directions, e.g., in two orthogonal coordinates along x and y axes. Muons pass through the volume or region of interest to be imaged and are scattered to an extent dependent upon the material occupying the volume or region of interest through which the muons pass. Another set of two or more planes of position-sensitive muon detectors can record outgoing muon positions and directions. The muon detectors (e.g., drift tubes) in the detectors can be arranged to allow at least three charged particle positional measurements in a first direction and at least three charged particle positional measurements in a second direction which is different from the first direction and may be orthogonal to the first direction. Side detectors (not shown) positioned at opposing locations near the volume or region of interest may be used to detect more horizontally or lateral orientated muon tracks. The scattering angle of each muon is computed from the incoming and outgoing measurements.

The exemplary muon tomography detection system can include a signal processing unit, e.g., a computer, to receive data of measured signals of the incoming or entering muons and outgoing or exiting muons from correspondingly positioned detectors. This signal processing unit can analyze the scattering of the muons in the volume or region of interest based on the measured incoming and outgoing positions and directions of muons to obtain a tomographic profile or the spatial distribution of the scattering density reflecting the scattering strength or radiation length within the volume or region of interest. The obtained tomographic profile or the spatial distribution of the scattering density within the volume or region of interest can provide reveal the internal makeup (e.g., anatomical structures of the subject) in the volume or region of interest. In some implementations, the muon detectors can be located above and below the volume or region of interest. In some implementations, additional muon detectors can be implemented on the lateral sides of the volume or region of interest to form a box or four sided detector structure that surrounds the volume or region of interest.

In processing the measurements associated with the muons in a volume or region of interest being imaged (e.g., body of a subject), the signal processing unit can reconstruct the trajectory of a muon through the volume or region of interest, measure the momentum of an incoming muon based on signals from the incoming muon detectors, measure the momentum of an outgoing muon based on signals from the outgoing muon detectors, and determine the spatial distribution of the scattering density of the volume or region of interest. These and other processing results can be used to construct the tomographic profile and measure various properties of the volume or region of interest.

For example, the reconstruction of the trajectory of a muon particle passing through a detector can include (a) receiving hit signals representing identifiers of sensors in the detector hit by charged particles and corresponding hit times; (b) grouping in-time sensor hits identified as being associated with a track of a particular charged particle passing through the detector; (c) initially estimating time zero for the particular charged particle; (d) determining drift radii based on estimates of time zero, drift time conversion data and the time of the hit; (e) fitting linear tracks to drift radii corresponding to a particular time-zero; and (f) searching and selecting a time-zero value associated with the best of the track fits performed for particular charged particle and computing error in time-zero and tracking parameters. Such reconstruction of the track based on the time zero fit provides a reconstructed linear trajectory of the charged particle passing through the charged particle detector without having to use fast detectors (such as photomultiplier tubes with scintillator paddles) or some other fast detector which detects the passage of the muon through the apparatus to the nearest few nanoseconds to provide the time-zero.

In another example, the processing for measuring the momentum of an incoming or outgoing muon based on signals from the corresponding incoming or outgoing detectors can include (a) configuring position sensitive detectors to scatter a charged particle passing though the detectors; (b) measuring the scattering of a charged particle in the position sensitive detectors, with the measuring the scattering including obtaining at least three positional measurements of the scattering charged particle; (c) determining at least one trajectory of the charged particle from the positional measurements; and (d) determining at least one momentum measurement of the charged particle from the at least one trajectory. This technique can be used to determine the momentum of the charged particle based on the trajectory of the charged particle which is determined from the scattering of the charged particle in the position sensitive detectors themselves without the use of additional metal plates in the detector.

In yet another example, the spatial distribution of the scattering density of the volume or region of interest can be determined from charged particle tomographic data by: (a) obtaining predetermined charged particle tomography data corresponding to scattering angles and estimated momentum of charged particles passing through the volume or region of interest; (b) providing the probability distribution of charged particle scattering for use in an expectation maximization (ML/EM) algorithm, the probability distribution being based on a statistical multiple scattering model; (c) determining substantially maximum likelihood estimate of object volume density using the expectation maximization (ML/EM) algorithm; and (d) outputting reconstructed object volume scattering density. The reconstructed object volume scattering density can be used to identify the internal structure of the volume or region of interest from the reconstructed volume density profile. Various applications include cosmic ray-produced muon tomography for medical imaging and radiation therapy.

As a muon traverses matter, it encounters Coulomb forces from each nucleon it passes and is deflected by the Coulomb forces. Each muon can be measured to provide the scattering angle of the muon trajectory as a measure of the integrated nuclear density along its path, the thickness of the material through which the muon has passed based on the distance of closest approach between linear extrapolations of the trajectory of the muon as it enters and leaves the volume or region of interest, and the location along the muons path where the scattering occurred as the point of closest approach between linear extrapolations of the muon's trajectory as it entered and left the volume or region of interest. Three-dimensional representations of the nuclear density in the volume or region of interest are generated from muon scattering data. The resolution of this reconstruction is determined by the number of muons passing through each resolution element (voxel).

Ambiguity in attribution of scattering signal to appropriate voxel neighborhoods produces consistent effects at discrete exposure times, but is not easily characterized over time. One solution is to develop independent background models for discrete exposure times. Exposure time dependent background models can then be subtracted from a reconstruction being performed on a volume or region of interest.

For each discrete exposure time, a set of background reconstructions can be built based on scans of innocuous scenes. This background set should include as many reconstructions of innocuous scenes as possible, but is effective with as few as 50-100 scanned scenes. Different ways of combining the information from the background dataset can be implemented. Examples include building the background model by averaging each voxel's reconstructed value from each reconstruction in the background dataset, finding the median reconstructed value, and finding the 95th percentile value. The background model can be built based on prior knowledge by either using a modeled reconstruction or using a measured reconstruction of an innocuous scene such as an empty volume or region of interest.

To properly combine the results of scans of innocuous scenes into a background model, the position and orientation of the scanned volume or region of interest must be known relative to the scanner coordinate system. The precision of this measurement needs to be of the same order as the expected resolution of the muon tracking in the volume of interest.

Once a background model is developed, the subtraction can be performed in the imaging processing. The value of a voxel in the background model is subtracted from the reconstructed value for that voxel in a considered scene. Thresholds are applied to the background subtracted scattering densities and the probability of the presence of a given structure in the volume of interest is calculated from the number of and the degree to which voxels are found over threshold.

Computationally fast reconstructions of muon tomography data can be performed by information provided by the closest approach point between the incoming and outgoing trajectories (PoCA), the closest approach distance between incoming and outgoing trajectories (DoCA) and the angle between the incoming and outgoing trajectories. The covariance of the angle and the DoCA can be used to calculate the thickness of the material.

The trajectory information of muons can be used to determine the thickness of materials based on muon tomography. Arrays for each voxel along the incoming and outgoing trajectories symmetrically around the PoCA position according to the calculated thickness are appended with a value that depends on the scattering angle. After the entire muon dataset is considered, the median is taken of the array for each voxel and that value assigned for the reconstruction.

During an exemplary charged particle therapy procedure, if the location and type of the target tissue (e.g., tumor) require the beam energy to be high enough so that partial charged particle flux can go through the incoming charged particle detector 120a and subsequently through patient body and reach the surface of the bottom charged particle detector 120b, then the dual head charged particle tomography scanner unit 120 can provide track information of the charged particles. The charged particle tomography scanner unit 120 can detect the charged particle beam energy loss and the individual track orientation changes between the incoming and outgoing detectors 120a and 120b, and provide such detected signals to the processing unit 220. Notably, the direct measurement of the charged particle tracks makes it possible for the system 200 to use both the detected stop tracks and through tracks of the charge particles to generate an energy deposition volumetric image.

In some implementations of the system 100, for example, the surface landmarks 199 are used to register the high quality anatomical image acquired at the therapy planning stage to the scatter image by adopting a surface landmark based registration algorithm or a volumetric image based registration algorithm. For example, this can provide an additional guidance map (which can be used with scatter image reconstruction together) for stop image reconstruction.

If the beam energy used for the charged particle radiation therapy is too low and does not allow sufficient particles to go through the patient body, for example, then the charged particle therapy unit 110 can apply a small fraction of the therapy dose with higher energy (e.g., enough to allow particles to go through the patient body) for creating a scatter image before performing the therapy procedure.

In some instances such as electron therapy, for example, where the electron energy only allows them to go through a very finite range, the incoming detector 120a can be used as the only detector to measure the incident tracks and create the stop image. But additional registration methods, e.g., such as optical/ultrasound/X-ray based registration methods, can be provided for the same anatomical region to allow the planning images to be registered for stop image reconstruction.

In some implementations, for example, iterative image reconstruction or hybrid image reconstruction algorithms (combining the scatter image and stop image recon) allows both the energy deposition measurement and the scatter information to be used in the image reconstruction.

Implementations of the subject matter and the functional operations described in this patent document and attached appendices can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document and attached appendices contain many specifics, these should not be construed as limitations on the scope of any invention or of what may be claimed, but rather as descriptions of features that may be specific to particular embodiments of particular inventions. Certain features that are described in this patent document and attached appendices in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendices should not be understood as requiring such separation in all embodiments.

Only a few implementations and examples are described and other implementations, enhancements and variations can be made based on what is described and illustrated in this patent document and attached appendices.

What is claimed are techniques and structures as described and shown, including:

1. A method for monitoring volumetric radiation dose in a medical application, comprising:
   delivering, from a charged particle delivery system, a charged particle beam of charged particles toward a region of interest of a subject, the region of interest including a tissue or organ of a human subject, the charged particle delivery system configured to direct at least a portion of the charged particle beam to the region of interest, wherein the charged particle beam is delivered after a pre-determined energy level of the charged particles is reached;
   detecting, by an incoming charged particle detector, at least some of the charged particles passing through the incoming charged particle detector and entering the region of interest of the subject;
   generating, by the incoming charged particle detector, a signal associated with the detected charged particles passing through the incoming charged particle detector and entering the region of interest of the subject;
   detecting, by an outgoing charged particle detector, at least some of the charged particles passing through and exiting the region of interest of the subject;
   controlling at least one characteristic of the charged particle beam delivered by the charged particle delivery system based on the signals associated with the detected charged particles entering and exiting the region of interest of the subject;
   generating, by the outgoing charged particle detector, a signal associated with the detected exiting charged particles;
   monitoring, in real time, a radiation dose of the region of interest of the subject based on the signals associated with the detected charged particles entering and exiting the region of interest of the subject; and
   generating an image of the region of interest based on the signals associated with the detected charged particles entering and exiting the region of interest of the subject in real time, wherein the image is generated by combining any two or more types of:
      measured data of trajectory changes of the at least some of the charged particles passing through and exiting the region of interest of the subject,
      information on stopped charged particles trapped inside the region of interest of the subject, and
      information on energy loss of the at least some of the charged particles passing through and exiting the region of interest of the subject.

2. The method of claim 1, wherein:
   detecting the at least some of the charged particles passing through the incoming charged particle detector and entering the region of interest of the subject includes detecting trajectory information of the at least some of the charged particles passing through the incoming charged particle detector and entering the region of interest of the subject; and
   detecting the at least some of the charged particles passing through and exiting the region of interest of the subject includes detecting trajectory information of the at least some of the charged particles passing through and exiting the region of interest of the subject.

3. The method of claim 2, wherein the trajectory information of the at least some of the charged particles includes one or more of a momentum, an incident point location, or an incident angle of a given charged particle of the charged particle beam.

4. The method of claim 2, further comprising:
   determining the energy loss based on the at least some of the charged particles entering and exiting the region of interest of the subject and based on at least some of the charged particles being stopped inside the region of interest of the subject.

5. The method of claim 4, further comprising:
   generating a map of the radiation dose based on the determined energy loss.

6. The method of claim 5, wherein the map of the radiation dose is a three-dimensional radiation dose delivery volumetric image based on absolute energy deposition of the charged particles.

7. The method of claim 1, wherein the at least one characteristic includes a strength or a direction of the charged particle beam delivered by the charged particle delivery system.

8. The method of claim 1, further comprising:
   controlling movement of one or both of the incoming charged particle detector and the outgoing charged particle detector.

9. The method of claim 1, wherein the charged particles include protons, carbon ions, muons, or electrons.

10. The method of claim 1, wherein the incoming charged particle detector and the outgoing charged particle detector detect individual charged particles entering and exiting the region of interest of the subject.

11. A charged particle tomography and radiation therapy system, comprising:
    a charged particle delivery system configured to deliver a charged particle beam of charged particles toward a region of interest of a subject, the region of interest including a tissue or organ of a human subject, the charged particle delivery system configured to direct at least a portion of the charged particle beam to the region of interest,
       wherein the charged particle delivery system includes an accelerator configured to store the charged particles and accelerate the stored charged particles to a pre-determined energy level, and
       wherein the accelerator is configured to deliver the charged particle beam after the pre-determined energy level of the charged particles is reached;
    a charged particle tomography scanner (CPTS) unit to detect at least some of the charged particles of the charged particle beam delivered to the region of interest of the subject, the CPTS unit including:
       an incoming charged particle detector positioned at a location near the region of interest of the subject to detect at least some of the charged particles passing through the incoming charged particle detector and entering the region of interest of the subject,
          wherein the incoming charged particle detector is configured to generate a signal associated with the detected charged particles passing through the incoming charged particle detector and entering the region of interest of the subject, and an outgoing charged particle detector positioned at a location near the region of interest of the subject opposite to the location of the entering charged particle detector to detect at least some of the charged particles passing through and exiting the region of interest of the subject, wherein the outgoing charged particle detector is configured to generate a signal associated with the detected exiting charged particles;

a processing unit in data communication with the CPTS unit, the processing unit configured to:

control at least one characteristic of the charged particle beam delivered by the charged particle delivery system based on the signals associated with the detected charged particles entering and exiting the region of interest of the subject;

monitor, in real time, a radiation dose of the region of interest of the subject based on the signals associated with the detected charged particles entering and exiting the region of interest of the subject; and generate an image of the region of interest based on the signals associated with the detected charged particles entering and exiting the region of interest of the subject in real time, wherein the image is generated by combining any two or more types of:

measured data of trajectory changes of the at least some of the charged particles passing through and exiting the region of interest of the subject, information on stopped charged particles trapped inside the region of interest of the subject, and information on energy loss of the at least some of the charged particles passing through and exiting the region of interest of the subject.

12. The system as in claim 11, wherein the at least one characteristic includes a strength or a direction of the charged particle beam delivered by the charged particle delivery system.

13. The system as in claim 11, wherein the processing unit is configured to:

detect the at least some of the charged particles passing through the incoming charged particle detector and entering the region of interest of the subject includes detecting trajectory information of the at least some of the charged particles passing through the incoming charged particle detector and entering the region of interest of the subject; and detect the at least some of the charged particles passing through and exiting the region of interest of the subject includes detecting trajectory information of the at least some of the charged particles passing through and exiting the region of interest of the subject.

14. The system as in claim 13, wherein the trajectory information of the at least some of the charged particles includes one or more of a momentum, an incident point location, or an incident angle of a given charged particle of the charged particle beam.

15. The system as in claim 13, wherein the processing unit is further configured to:

determine the energy loss based on the at least some of the charged particles entering and exiting the region of interest of the subject and based on at least some of the charged particles being stopped inside the region of interest of the subject.

16. The system as in claim 15, wherein the processing unit is further configured to:

generate a map of the radiation dose based on the determined energy loss.

17. The system as in claim 16, wherein the map of the radiation dose is a three-dimensional radiation dose delivery volumetric image based on absolute energy deposition of the charged particles.

18. The system as in claim 11, further comprising:

a motion control unit configured to control movement of one or both of the incoming charged particle detector and the outgoing charged particle detector.

19. The system as in claim 11, wherein the charged particles include protons, carbon ions, muons, or electrons.

20. The system as in claim 11, wherein the incoming charged particle detector and the outgoing charged particle detector are configured to detect individual charged particles entering and exiting the region of interest of the subject.

* * * * *